United States Patent [19]

Walker et al.

[11] 4,211,719

[45] Jul. 8, 1980

[54] CATALYTIC PROCESS FOR POLYHYDRIC ALCOHOLS AND DERIVATIVES

[75] Inventors: Wellington E. Walker, Charleston; David R. Bryant; Earle S. Brown, Jr., both of South Charleston, all of W. Va.

[73] Assignee: Union Carbide Corporation, New York, N.Y.

[21] Appl. No.: 9,352

[22] Filed: Feb. 5, 1979

Related U.S. Application Data

[63] Continuation of Ser. No. 877,589, Feb. 13, 1978, abandoned, which is a continuation-in-part of Ser. No. 712,152, Aug. 16, 1976, abandoned, which is a continuation-in-part of Ser. No. 488,139, Jul. 12, 1974, abandoned.

[51] Int. Cl.$^2$ .................. C07C 27/06; C07C 29/16
[52] U.S. Cl. ............................ 260/449 L; 260/449 R; 260/449.5; 252/431 R; 252/431 N; 252/431 P; 252/431 L
[58] Field of Search ............ 260/449 R, 449 L, 449.5; 252/431 R, 431 N, 431 P, 431 L

[56] References Cited

U.S. PATENT DOCUMENTS

| 3,576,881 | 4/1971 | Senn .................... 260/604 |
| 3,725,534 | 4/1973 | Reisch ................. 260/604 HF X |
| 3,833,634 | 9/1974 | Pruett et al. ........ 260/449 R |
| 3,940,432 | 2/1976 | Walker et al. ...... 260/449 R |
| 3,957,857 | 5/1976 | Pruett et al. ........ 260/449 R |

OTHER PUBLICATIONS

Martinengo et al., Gazz, 102, (1972), 344–354.

*Primary Examiner*—Howard T. Mars
*Attorney, Agent, or Firm*—Marylin Klosty

[57] ABSTRACT

This invention relates to the manufacture of such valuable chemicals as polyhydric alcohols, their ether and ester derivatives, oligomers of such alcohols and monohydric alcohols and their ether and ester derivatives by reacting oxides of carbon and hydrogen in the presence of a quaternary ammonium cation and a rhodium carbonyl complex provided to the reaction as a rhodium carbonyl cluster anion which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ and said cation is present in the reaction mixture in about 0.8 to about 2.0 moles of cation for every six rhodium atoms present in the reaction mixture.

10 Claims, No Drawings

CATALYTIC PROCESS FOR POLYHYDRIC ALCOHOLS AND DERIVATIVES

BACKGROUND OF THE INVENTION

This application is a continuation of our prior U.S. application: Ser. No. 877,589 filed Feb. 13, 1978, now abandoned, which is a continuation-in-part of application Ser. No. 712,152 filed Aug. 16, 1976, now abandoned, which is a continuation-in-part of application Ser. No. 488,139 filed July 12, 1974, now abandoned.

This invention is concerned with an improved process for the manufacture of polyhydric alcohols, their ether and ester derivatives, and oligomers of such alcohols. This invention also produces monohydric alcohols such as methanol, and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

It is known that monofunctional compounds such as methanol can be obtained by reaction between carbon monoxide and hydrogen at elevated pressures, e.g., up to about 1000 atmospheres, and temperatures ranging from 250° C. to 500° C., using mixtures of copper, chromium and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures up to 400° C., using certain hydrogenation catalysts as exemplified by cobalt-containing compounds. U.S. Pat. Nos. 2,534,018; 2,570,792 and 2,636,046 are substantially similar in disclosure to the above said British patent. The only catalysts employed in the numbered examples of said U.S. Pat. No. 2,636,046 are those which contain cobalt.

It is also well-known that nickel is predominantly a catalyst for synthesis and for reforming methane according to the reaction

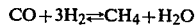

which proceeds from left to right at temperatures below about 500° C. and in the opposite direction at higher temperatures; see Kirk-Othmer, Encyclopedia of Chemical Technology, Second Edition, Volume 4, pages 452–453, John Wiley and Sons, New York (1964).

In copending application Ser. No. 219,130, filed Jan. 19, 1972, now U.S. pat. No. 3,833,634, and Belgium Pat. No. 793,086, published June 20, 1973, there is disclosed a process for the preparation of polyhydric alcohols by contacting a mixture of carbon monoxide and hydrogen with a catalytic amount of rhodium in complex combination with carbon monoxide.

U.S. Pat. No. 3,957,857 characterizes an improvement on the invention of Serial No. 219,130. There is disclosed in U.S. Pat. No. 3,957,857 a process for manufacturing polyhydric alcohols, their ether and ester derivatives, oligomers of such alcohols and monohydric alcohols and their ether and ester derivatives by reacting the oxides of carbon and hydrogen in the presence of a rhodium carbonyl complex which is provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ at a pressure of at least about 500 pounds per square inch, in association with a counter-ion. Suitable counter-ions for the cluster are a variety of metals and organic compounds. Included as organic counter-ions are the quaternary ammonium salts.

This invention is directed to a process for making polyhydric aliphatic alcohols and their ether, ester, and oligomer derivatives, such as alkane polyols, most specifically, alkane diols and triols, containing 2 or 3 carbon atoms, their ether, ester and oligomer derivatives.

As with the process of U.S. Pat. No. 3,957,857, a byproduct of this invention is the manufacture of the lesser valuable, but valuable nevertheless, monohydric alkanols such as methanol, ethanol, and propanol, and their ether and ester derivatives. The products of this invention contain carbon, hydrogen and oxygen.

The present invention is concerned with an improved and more stable catalyst system which enhances the production of polyhydric alcohols, their ether and ester derivatives, oligomers of such alcohols, monohydric alcohols and their ether and ester derivatives at lower catalyst concentrations, contact times, and operating temperatures and pressures. The improved catalyst system of the present invention involves reacting the oxides of carbon and hydrogen in the presence of a quaternary ammonium cation and a rhodium carbonyl complex which is provided to the reaction as a rhodium carbonyl cluster which possesses an infrared spectrum which exhibits three intense wavelength bands between about plus and minus 10 cm$^{-1}$ of about 1868 cm$^{-1}$ about 1838 cm$^{-1}$ and 1785 cm$^{-1}$ at a pressure of at least about 500 pounds per square inch absolute. The quaternary ammonium cation is present in the reaction mixture in an amount of about 0.8 to about 2.5 moles of cation for every six atoms of rhodium present in the reaction mixture.

The rhodium carbonyl cluster of this invention exhibits the above infrared spectrum either during the reaction or at a temperature and/or pressure below that at which the reaction is effected. In both instances, the catalytic effect is achieved suggesting that the characterized rhodium clusters are always present.

The quaternary ammonium cations useful in the present invention include those of the formula:

wherein $R_1$, $R_2$, $R_3$, and $R_4$ are either a straight or branched chain alkyl group, having from 1 to 20 carbon atoms in the alkyl chain, such as methyl, ethyl, n-propyl, isopropyl, n-butyl, octyl, 2-ethyl hexyl, dodecyl, and the like; or a cycloaliphatic group including the monocyclic and bicyclic groups cyclopentyl, cyclohexyl, and bicyclo-[2.2.1]heptyl groups, and the like; or an aryl, alkylaryl, or araalkyl group such as phenyl, naphthyl, xylyl, tolyl, t-butylphenyl, benzyl, beta-phenylethyl, 3-phenylpropyl, and the like; or a functionally substituted alkyl such as beta-hydroxyethyl, ethoxymethyl, ethoxyethyl, phenoxyethyl and the like; or a polyalkylene ether group of the formula $-C_nH_{2n}O)_x-$ $-OR$ wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like.

P. Chini, in a review article entitled "The Closed Metal Carbonyl Clusters" published in Reviews (1968), Inorganica Chemica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster". The rhodium carbonyl cluster compounds of this invention contain rhodium bonded to rhodium or rhodium bonded to another metal, such as cobalt, and/or iridium. The preferably rhodium carbonyl cluster compounds of this invention are those which contain rhodium-rhodium bonds. These compounds desirably contain carbon and oxygen in the form of carbonyl (—C—O), in which the carbonyl may be "terminal", "edge bridging", and/or "face bridging". They may also contain hydrogen and carbon in forms other than carbonyl. Illustrative of two distinct rhodium carbonyl clusters which are suitable for use in this invention are those shown, for example, in aforementioned U.S. Pat. No. 3,957,857 at column 2, lines 54–67 and column 3, lines 1–17.

The structures of the rhodium carbonyl clusters may be ascertained by X-ray crystal diffraction, nuclear magnetic resonance, spectra, NMR, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chemica Acta, 3:2 pp 299–302, June (1969). Of particular analytical utility in the present is the use of infrared spectroscopy which allows for qualitative and what is presently believed to be a quantitative characterization of the particular rhodium carbonyl cluster present during the operation of the process of the present invention.

Rhodium carbonyl cluster ions which possess the infrared spectrum characterized previously, function in association with oxides of carbon and hydrogen, as herein defined, to produce the polyhydric alcohols, etc. The exact mechanism by which the cluster compounds act to catalyze the reaction is not fully appreciated at this time. It is believed that the reaction is dependent upon the existence of the following equilibria:

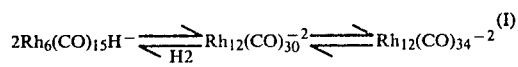

Such an equilibria may be in situ formed from a less complex rhodium carbonyl compound or a more complexed rhodium carbonyl compound. However, it may be that such cluster equilibria is symtomatic of an intermediate transitory rhodium carbonyl structure which serves to radicalize two molecules of carbon monoxide which are subsequently converted to the polyhydric alcohol.

In practicing the present invention the rhodium carbonyl cluster catalyzed reaction of carbon monoxide and hydrogen is carried out in the presence of about 0.8 to about 2.0 moles, preferably in about 1.10 to about 1.60 moles, and more preferably in about 1.3 to about 1.40 moles of quaternary ammonium cation for every six atoms of rhodium present in the reaction mixture.

The precise role of the quaternary ammonium cation in the reaction of carbon monoxide and hydrogen catalyzed by the rhodium carbonyl clusters to produce polyhydric alcohols is not clearly understood. The reaction is believed to involve the reaction of carbon monoxide with the active catalytic species to form a radical of CO which may or may not require the addition of another radical of CO prior to hydrogenation to form the polyhydric alcohol or methanol. Infrared analysis shows that under reaction conditions which favor the production of polyhydric alcohols, the characteristic 3 band pattern of the $[Rh_{12}(CO)_{34}]^{2-}$ cluster is present; while under conditions which favor the production of methanol, only the single band pattern, about 1900 cm$^{-1}$, of the monomeric $Rh(CO)_4$ anion is dominant and the aforementioned 3 band pattern is missing of minimized in intensity.

The use of about 0.8 to about 2.0 moles of quaternary ammonium cation for every six atoms of rhodium present in the reaction mixture allows for the production of polyhydric alcohols at lower operating pressures with no reduction of product yield for a given set of reaction conditions. When the amount of quaternary ammonium cation in the reaction is greater or less than this amount, the productivity and efficiency of reaction to polyhydric alcohol is significantly reduced and the reaction conditions required to achieve results remotely comparable are much more stringent and costly.

In view of the fact that the quaternary ammonium cation does not enter into the reaction, and it has not been clearly established to be necessary for catalyst formation, the presence of this select amount of the cation for optimum catalysis when the counter-ion is a quaternary ammonium cation is not clearly understood. In terms of the results achieved, it would appear that such select amount of the quaternary ammonium cation functions in a manner which may reduce factors which inhibit the aforementioned CO radical formation.

The rhodium carbonyl complex is, as characterized above, a rhodium containing compound in which the rhodium values are complexed with CO. This can be achieved with just CO, hydrogen and the quaternary ammonium cation, or there may be included other organic materials to create the complex. In the last case "complex" means a coordination compound formed by the union of one or more electronically rich organic molecules or atoms capable of independent existence with one or more electronically poor molecules or atoms, each of which is also capable of independent existence. These organic rhodium cluster complexes are derived from the association of organic ligands or organic counter-ions with rhodium carbonyl solutions.

Organic ligands which are suitable in the practice of the invention contain at least one nitrogen atom (hereinafter call Lewis base nitrogen atom) and/or at least one oxygen atom (hereinafter called Lewis base oxygen atom), said atoms possessing a pair of electrons available for the formation of coordinate bonds with rhodium. Suitably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 1 and upwards to 4 Lewis base atoms, preferably from 1 to 3 such atoms, and most preferably 1 or 2 Lewis base atoms. These organic ligands are said to be multidentate or polydentate, that is to say, such ligands are bidentate, tridentate, or quadridentate, depending on whether 2, 3, or 4 Lewis base atoms are involved in the formation of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

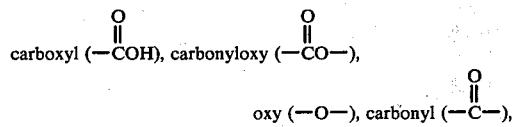
carboxyl (—COH), carbonyloxy (—CO—), oxy (—O—), carbonyl (—C̈—), etc., all of said groups containing Lewis base oxygen atoms. In this respect, it is the "hydroxyl" oxygen in the

—COH group and the "oxy" oxygen in the

—CO— group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylendiamine, N,N,N',N-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo [2.2.2] octane, methyl-substituted 1,4-diazabicyclo [2.2.2] octaine, purine, 2-amino-pyridine, 2-(dimethylamino) pyridine, 1,10-phenan-throline, methyl-substituted 1,10-phenanthroline, 2-(dimethylamino)-6-methoxyquinoline, 7-chloro-1, 10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, diglycolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenezene, 1,2-diethoxybenzene, methyl acetate, ethanol, 1,2-dimethoxyethane, 1,2-diethoxyethane, 1,2-d-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other organic counter-ions are formed by ionic association with the rhodium carbonyl cluster ions. They are from organic compounds which possess Lewis base nitrogen atoms and typically are composed or carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, tri-n-butylamine, dibutylamine, methylamine, dodecylamine, morpholine, aniline, benzylamine, octadecylamine, naphthylamine, cyclohexylamine, and the like.

In the practice of the present invention a normally liquid organic solvent is employed in an amount sufficient to maintain a homogeneous reaction mixture containing the cluster and the quaternary ammonium cation. Illustrative of the solvents which are generally suitable in the practice of the present invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc; ethers such as tetrahydrofuran, tetrahydropyran, diethyl ether, 1,2-dimethoxybenzene, 1,2-ethoxybenzene, the mono- and dialkyl ethers of alkylene glycols and polyalkylene glycols, such as ethylene glycol, of propylene glycol, of butylene glycol, of diethylene glycol, of dipropylene glycol, of triethylene glycol, of tetraethylene glycol of pentaethylene glycol, of dibutylene glycol, of oxyethyleneoxypropylene glycol, etc., preferably, those in which the alkylene group contains 2 carbon atoms in the divalent moeity, such as, ethylene and 1,2-propylene; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethyl-hexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; lactones such as $\gamma$-butyrolactone and $\delta$-valerolactone, etc.; and others. $\gamma$-butyrolactone and the mono and dialkyleters of triethylene and tetraethylene glycol are the preferred solvents in the practice of the present invention.

It should be noted that the use of reactive solvents in the practice of desirable embodiments of the invention can give rise to a range of useful products. For instance, the mono and diacetate esters of ethylene glycol can be obtained by using acetic acid as the solvent in the reaction medium. The use of alkanols, e.g., methanol and ethanol, can result in the monoalkyl ethers of ethylene glycol.

In one of the embodiments of the present invention the quaternary ammonium cation is provided to the reaction mixture in its simple salt form. Suitable salts useful in the present invention include those of the general formula R'X wherein R' may be any of the quaternary ammonium cations defined by formula (II) above and X may be hydroxide; a halogen, such as fluorine, chlorine, bromine and iodine; a carboxylate group, such as formate, acetate, propionate and butyrate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolinolate group; and others. These quaternary ammonium salts may be prepared by any of the methods well known in the art.

In another embodiment of the present invention the quaternary ammonium salt is added to the reaction mixture as the preformed dodecarhodium triaconta carbonyl salt of the formula $(R'_4N)_2Rh_{12}(CO)_{30}$ wherein R' may have any of the values of $R_{1-4}$ defined in formula (II) above. These salts may be prepared by dissolving the sodium salt of dodecarhodium triaconta carbonyl, $Na_2[Rh_{12}(CO)_{30}]$, in a sufficient amount of a suitable solvent such as tetrahydrofuran and then adding the desired quaternary ammonium acetate salt, e.g., slightly in excess of the stoichiometric amount. The mixture is stirred from about 2 to about 30 minutes at 20° C. to about 75° C. then water is added in a sufficient amount (from about 50 to about 200 percent by weight of the solvent) to crystallize out the quaternary ammonium dodecarhodium triaconta carbonyl salt, $(R'_4N)_2Rh_{12}(CO)_{30}$.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. No particular advantages at the relatively high concentrations of rhodium are manifest. Depending on various factors such as the cation of choice, the partial pressures of oxides of carbon and hydrogen, the total operative pressure of the system, the operative temperature, the choice of the normally-liquid organic solvent, and other considerations, a catalyst concentration of from about $1 \times 10^{-5}$ to about $1 \times 10^{-1}$ weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Suitable operative temperatures are between about 150° C. to about 300° C., preferably from about 190° C. to about 275° C., and more preferably about 190° C. to about 240° C.

The equilibrium reaction for forming ethylene glycol is:

$$2\,CO + 3H_2 \rightleftharpoons HOCH_2CH_2OH$$

At relatively high temperatures the equilibrium increasingly favors the left hand side of the equation. In the practice of the present invention, to drive the reaction to the formation of a fixed increased quantity of ethylene glycol, lower partial pressures of carbon monoxide and hydrogen are required than those taught by the prior art.

This novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. However, at pressures greater than about 15,000 psia no improvement in the productivity of polyhydric alcohol can be attributed to the presence of the quaternary ammonium cations in select amounts. This non-beneficial effect of the cation at high pressures is believed due to the overriding effect the increased pressure of carbon monoxide has on the stability of the rhodium carbonyl cluster. A suitable pressure range for effecting the novel process is from about 1000 psia, to about 15,000 psia, preferably about 2000 psia to about 12,000 psia, and more preferably about 6,000 psia to about 10,000 psia. The pressures referred to above represent the total pressure of hydrogen and oxides of carbon.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods wellknown in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

The active forms of the rhodium carbonyl clusters may be prepared by various techniques. They can be preformed as indicated previously and then introduced into the reaction zone. Alternatively, any of the host of rhodium-containing substances as well as the cation forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide, $(Rh_2O_3)$, tetrarhodium dodecacarbonyl, dirhodium octacarbonyl, hexarhodium hexadecacarbonyl $(Rh_6(CO)_{16})$, rhodium (II) formate, rhodium (II) acetate, rhodium (II) propionate, rhodium (II) butyrate, rhodium (II) valerate, rhodium (III) naphthenate, rhodium dicarbonyl acetylacetonate, rhodium tris(acetyoacetonate), rhodium trihydroxide, indenylrhodium dicarbonyl, rhodium dicarbonyl (1-phenylbutane-1,3-dione), tris (hexane-2,4-dionato)rhodium (III), tris(heptane-2,4-dionato)rhodium(III), tris (1-phenylbutane-1,3-dionato)rhodium(III), tris(3methylpentane-2,4-dianato(rhodium(III) and tris(1-cyclohexylbutane-1,3-dionato(rhodium(III).

The preparation of rhodium carbonyl cluster compounds is conveniently carried out in a diluent or mixture of diluents, e.g., benzene. Tetrarhodium dodecacarbonyl, though of limited solubility, can be added to the diluent in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30° C. to about 100° C., for a period of time ranging from minutes to a few days, generally from about 30 minutes to about 24 hours. The resulting rhodium cluster compound contained in the organic diluent is catalytically active in this process. The compound contains rhodium in clustered combination with carbon monoxide and the counter ion of choice.

The equipment arrangement and procedure which provides the capability for determining the existence of rhodium carbonyl clusters having the aforedefined infrared spectrum characteristics, during the course of the manufacture of polyhyric alcohols from carbon monoxide and hydrogen, pursuant to this invention, is disclosed and schematically depicted in U.S. patent application, Ser. No. 462,109, filed Apr. 18, 1974, now U.S. Pat. No. 3,957,857 the disclosure of which is incorporated herein by reference.

A particularly desirable infrared cell construction is described in copending U.S. patent application, Ser No. 451,437, filed Mar. 15, 1974 now U.S. Pat. No. 3,886,364 and its disclosure of a preferred cell construction is incorporated herein by reference.

The "oxide of carbon" is covered by the claims and as used herein is intended to mean carbon monoxide and mixtures of carbon dioxide and carbon monoxide, either introduced as such or formed in the reaction.

The following examples are merely illustrative and are not preferred as a definition of the limits of the invention.

EXAMPLE 1

A 150 ml. capacity stainless steel reactor capable of withstanding pressures up to 7,000 atomspheres was charged with a premix of 75 cubic centimeters (cc) of the dimethylether of tetraethylene glycol (tetraglyme) 3.0 millimoles (mmol) 0.8 gms, of rhodium dicarbonylacetylacetonate ($Rh(CO)_2AcAc$), 10 millimoles (mmol) of distilled 2-hydroxypyridine. The reactor was sealed and charged with a gaseous mixture, containing equal molar amounts of carbon monoxide and hydrogen, to a pressure of 8,000 pounds per square inch (psig). Heat was applied to the reactor and its contents, when the temperature of the mixture inside the reactor reached 190° C., as measured by a suitably placed thermocouple, an additional adjustment of carbon monoxide and hydrogen ($H_2:CO = 1:1$ mole ratio) was made to bring the pressure back to 8000 psig. The temperature was maintained at 200° for 4 hours. During this period of time additional carbon monoxide and hydrogen was added whenever the pressure inside the reactor dropped below about 7500 psig. With these added repressurizations the pressure inside the reactor was maintained at 8000 psig±400 psig over the entire 4 hour period.

After the 4 hours period, the vessel and it conents was cooled to room temperature, the excess gas vented and the reaction product mixture was removed. Analysis of the reaction product mixture was made by gas chromatographic analysis using a Hewlitt Packard FM TM 810. The gas chromatograph is held at 50° for 2 minutes after introduction of two microliters of product sample and then programmed from 50° to 280° C. at 15° C. per minute.

Analysis of the product mixture shows 2.1 grams of methanol, 1.0 grams of ethylene glycol, 0.15 grams of methyl formate, 0.02 grams of ethylanol, 0.03 grams of ethyleneglycol monoformate and the rhodium recovered was 75 percent based on the total rhodium charged to the reactor.

The amount of rhodium recovered from the reactor is determined by atomic absorption analysis of the reaction mixture after the hour hours of reaction time has lapsed and the unreacted gases are vented to the atmosphere. Atomic absorption analysis is run using a Perkin and Elmer Model 303 Atomic Absorption Spectrophotometer, sold by Perkin and Elmer or Norwalk, Conn. Rhodium recovered therefore would be the present of the total rhodium charged that is still soluble or suspended in the reaction mixture at the end of the four hour reaction time.

The same equipment and procedure used in Example 1 was used for Examples 2 through 10 except for the reactants and/or conditions specified. In Examples 2 through 10 the quaternary ammonium salt was charged with the solvent to the reactor.

TABLE I'

| Example | Promoter | Products, grams | | | | Rhodium Recovery |
| | | Ethylene Glycol | Methanol | Methyl Formate | Glycol Monoformate | |
| --- | --- | --- | --- | --- | --- | --- |
| 2 | $(CH_3)_4N^+F^-$ | 3.0 | 2.0 | .18 | .09 | 83 |
| 3 | $(C_2H_5)_4N^+Cl^-$ | 2.0 | 2.0 | .15 | .05 | 90 |
| 4 | $(C_4H_9)_4N^+Cl^-$ | 2.2 | 2.02 | .16 | .07 | 82 |
| 5 | $(C_4H_9)_4N^+F^-$ | 2.2 | 2.05 | .17 | .04 | 80 |
| 6 | $(C_4H_9)_4N^+Br^-$ | 1.75 | 2.28 | .15 | .03 | 77 |
| 7 | $(C_4H_9)_4N^+I^-$ | 0.75 | 1.87 | — | 0.6 | — |
| 8 | Quat. UCON (a) | 1.15 | 2.3 | — | — | 81 |
| 9 | Quat. UCON (b) | 2.1 | 2.7 | — | .07 | 83 |
| 10 | Quat. UCON (c) | 2.3 | 2.2 | — | .08 | 87 |

(a) $(HOCH_2CH_2)_2(HOCH_2CH_2OCH_2CH_2)N^+(CH_2CH_2O^-)$
(b) Quaternized (Diisopropylamine containing ethylene oxide); molecular weight about 660
(c) Quaternized (Dimethylethanolamine containing ethylene oxide and propylene oxide); molecular weight about 2050
1. All runs at 8000 psig, 1:1 $H_2$/CO, 220° C., 4 hours reaction time, 75 cc Tetraglyme, 3.0 mm $Rh(CO)_2AcAc$, 10 mmol distilled 2-Hydroxypyridine, ~0.5 mmol quaternary ammonium salt.

EXAMPLE 11

The same equipment and procedure which was used in Example 1 was used in the present example except that the premix initially charged to the reactor consisted of 75 cc sulfolane and 3.0 millimoles (mmol) of $Rh(CO)_2AcAc$ (rhodium dicarbonylacetylacetonate). Ammonium acetate was added to the reactor at differing levels of concentration such that the ratio of moles of salt per six atoms of rhodium was varied as shown in Table A below. The gaseous mixture of hydrogen and carbon monoxide inside the reactor was maintained at 8000 psig over a 4 hour period while maintaining the temperature at 240° C.

Analysis of the product mixture for methanol and ethylene glycol is shown in Table A along with the percent rhodium recovery from the reactor.

Table A

| Moles of Salt/ 6 atoms Rh | Methanol (grams) | Ethylene Glycol (grams) | Rhodium Recovery (%) |
|---|---|---|---|
| 1.0 | 2.6 | 5.1 | 82 |
| 1.3 | 2.8 | 6.1 | 88 |
| 1.6 | 3.4 | 6.8 | 91 |
| 2.0 | 3.0 | 5.9 | 83 |
| 2.5 | 3.9 | 5.9 | 92 |
| 5.0 | 3.9 | 3.7 | 88 |

EXAMPLE 12

The procedure of Example 11 was repeated except that tetramethylammonium acetate was added to the reactor in varying concentrations instead of ammonium acetate. The analysis of the product mixture for each level of quaternary ammonium salt concentration is shown in Table B below.

Table B

| Moles of Salt/ 6 atoms Rh | Methanol (grams) | Ethylene Glycol (grams) | Rhodium Recovery (%) |
|---|---|---|---|
| 1.3 | 2.6 | 3.4 | 84 |
| 1.6 | 2.9 | 6.1 | 90 |
| 2.0 | 2.4 | 6.8 | 94 |
| 2.5 | 3.0 | 5.5 | 86 |
| 5.0 | 3.7 | 2.9 | 95 |

EXAMPLE 13

The procedure of Example 12 was repeated except that tetraethylammonium acetate was the quaternary ammonium salt added to the reactor. The data is shown in Table C below.

Table C

| Moles of Salt/ 6 atoms Rh | Methanol (grams) | Ethylene Glycol (grams) | Rhodium Recovery (%) |
|---|---|---|---|
| 1.3 | 3.4 | 0.9 | 77 |
| 1.6 | 3.7 | 2.4 | 89 |
| 2.0 | 3.0 | 4.8 | 86 |
| 2.5 | 2.9 | 5.5 | 91 |
| 3.0 | 3.1 | 5.1 | 90 |
| 5.0 | 3.7 | 3.3 | 95 |

What is claimed is:

1. In the process of making alkane polyols which comprises reacting at a pressure of from 1000 psia to about 15,000 psia and a temperature of about 100° C. to about 375° C., a mixture consisting essentially of oxides of carbon and hydrogen in the presence of a quaternary ammonium cation and a rhodium carbonyl complex, said complex being provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$, wherein the improvement comprises providing to the reaction mixture about 0.8 to about 2.5 moles of the quaternary ammonium cation for every six atoms of rhodium present in the reaction mixture, and said quaternary ammonium cation has the formula

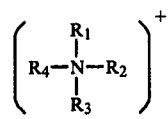

where $R_1$, $RHd_2$, $R_3$ and $R_4$ is a straight or branched chain alkyl having from one to 20 carbon atoms, a cycloaliphatic, aryl, alkylaryl or aralkyl group, or a polyalkylene ether group of the formula, —$(C_nH_{2n}O)_x$—OR, wherein n has an average value from 1 to 4, x has an average value from 2 to about 150, and R is hydrogen or alkyl having from 1 to 12 carbon atoms.

2. The process of claim 1 wherein the cation is present in the reaction mixture in about 1.10 to about 1.60 moles of cation for every six atoms of rhodium.

3. The process of claim 2 wherein the cation is present in the reaction mixture in about 1.2 to about 1.4 moles of cation for every six atoms of rhodium.

4. The process of claim 1 wherein the reaction is effected in the presence of an inert solvent.

5. The process of claim 4 wherein the solvent is a dialkyl ether of alkylene glycols or polyalkylene glycol.

6. The process of claim 5 wherein the solvent is the dimethylether of tetraethylene glycol.

7. The process of claim 1 wherein the temperature of the reaction is from about 150° C. to about 300° C.

8. The process of claim 7 wherein the temperature of the reaction is from about 190° C. to about 275° C.

9. The process of claim 8 wherein the temperature of the reaction is from about 190° C. to about 240° C.

10. The process of claim 1 wherein the reaction is conducted under a pressure ranging from about 2,000 pounds per square inch absolute to about 12,000 pounds per square inch absolute.

* * * * *

UNITED STATES PATENT AND TRADEMARK OFFICE
CERTIFICATE OF CORRECTION

PATENT NO. : 4,211,719
DATED : July 8, 1980
INVENTOR(S) : Walker et al.

It is certified that error appears in the above—identified patent and that said Letters Patent is hereby corrected as shown below:

Column 12, line 18, delete "hour" and replace with -- four --; line 23, delete "present" and replace with -- percent -- .

Signed and Sealed this

*Twenty-third* Day of *June 1981*

[SEAL]

*Attest:*

RENE D. TEGTMEYER

*Attesting Officer*      *Acting Commissioner of Patents and Trademarks*